United States Patent

Bruynes

[11] 4,347,358
[45] * Aug. 31, 1982

[54] CEPHALOSPORIN INTERMEDIATES

[75] Inventor: Cornelis A. Bruynes, Koudekerk an der Rijn, Netherlands

[73] Assignee: Gist-Brocades N.V., Delft, Netherlands

[*] Notice: The portion of the term of this patent subsequent to Jan. 8, 1997, has been disclaimed.

[21] Appl. No.: 126,127

[22] Filed: Feb. 29, 1980

[30] Foreign Application Priority Data

Mar. 6, 1979 [NL] Netherlands ............ 7901774

[51] Int. Cl.$^3$ .................................... C07D 501/20
[52] U.S. Cl. ............................ 544/016; 424/246; 544/30
[58] Field of Search .............. 544/16, 22, 28, 30; 424/246

[56] References Cited

U.S. PATENT DOCUMENTS 3,705,897 12/1972 Murphy ........................ 544/16
3,922,268 11/1975 Murphy et al. ............... 544/16
4,182,870 1/1970 Bruynes et al. ............... 544/16

FOREIGN PATENT DOCUMENTS 1149 3/1979 European Pat. Off. .
7004479 9/1970 Netherlands .
7012532 1/1980 Netherlands .

Primary Examiner—Nicholas S. Rizzo
Attorney, Agent, or Firm—Hammond, Littell, Weissenberger and Muserlian

[57] ABSTRACT

Novel bromo-substituted deacetoxycephalosporins of the formula

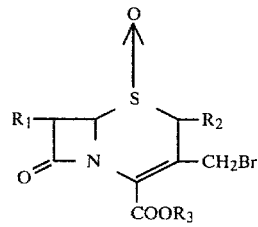

wherein $R_1$ is selected from the group consisting of benzamido, formamido, phenylacetamido and phenoxyacetamido, $R_2$ is selected from the group consisting of hydrogen and bromine and $R_3$ is a silyl group of the formula

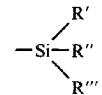

wherein R', R" and R''' are individually selected from the group consisting of alkyl of 1 to 6 carbon atoms, a halogen-substituted alkyl of 1 to 6 carbon atoms and aryl, which are suitable intermediates in processes for the preparation of antibiotics and their preparation.

14 Claims, No Drawings

CEPHALOSPORIN INTERMEDIATES

STATE OF THE ART

Dutch patent applications Ser. No. 70 04479, No. 70 12532 and No. 72 12992 describe compounds similar to compounds of formula I wherein $R_2$ is hydrogen and $R_3$ is an easily hydrolyzed ester group. Application Ser. No. 70 04479 describes carboxylic acid carbon esters and the other applications indicate the possibility of silyl protection of the said carboxylic acid group but has hardly ever been used and is not specifically named or produced therein.

OBJECTS OF THE INVENTION

It is an object of the invention to provide the novel bromo-substituted deacetoxycephalosporins of formula I.

It is another object of the invention to provide a novel process for the preparation of the compounds of formula I.

These and other objects and advantages of the invention will become obvious from the following detailed description.

THE INVENTION

The novel intermediate compounds of the invention are bromo-substituted deacetoxycephalosporins of the formula

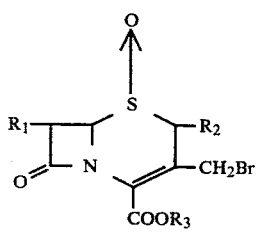

wherein $R_1$ is selected from the group consisting of benzamido, formamido, phenylacetamido and phenoxyacetamido, $R_2$ is selected from the group consisting of hydrogen and bromine and $R_3$ is a silyl group of the formula

wherein R', R", and R''' are individually selected from the group consisting of alkyl of 1 to 6 carbon atoms, a halogen-substituted alkyl of 1 to 6 carbon atoms and aryl. The substituents in the 1- and 7-positions are in the β-configuration.

The use of silyl protection in compounds of the type mentioned herebefore has clear advantages over the use of the conventional carbon protection, mainly because the protecting silyl group can be removed quite easily again, vis. by hydrolysis in situ, for example, directly after the replacement of the bromine atom in the 3'-position by another substituent has been effected as described in more detail herebelow.

The 3'-bromo-substituted compounds of formula I wherein $R_2$ is hydrogen are suitable intermediates in processes for the preparation of known and new antibiotics because the bromine atom in the 3'-position can be replaced in a known and usually simple manner by a nucleophilic substituent which substituents can not be introduced directly into the 3-methyl group of corresponding unsubstituted deacetoxycephalosporins.

The 2,3'-dibromo-substituted deacetoxycephalosporins of formula I wherein $R_2$ is bromine can be partially debrominated in a comparatively simple manner, thus replacing the bromine atom in the 2-position by a hydrogen atom as described in European patent application Ser. No. 78200174.7. Thus, the 2,3'-dibromo-substituted deacetoxycephalosporins of formula I can also be used after a preceding selective debromination, as intermediates in processes for the preparation of 3'-nucleophilic-substituted deacetoxycephalosporins.

The replacement of the bromine atom in the 3'-position in compounds of formula I (as the case may be, after previous removal of a bromine atom in the 2-position) by various types of nucleophilic groups, providing antibiotically valuable cephalosporins or intermediates for antibiotically valuable cephalosporins, has already been described extensively in the literature such as in Dutch patent application No 70 12532. Moreover, the compounds of formula I can also be used in processes for the preparation in conventional manner of new 3'-nucleophilic-substituted cephalosporins.

The process of the invention for the preparation of compounds of formula I comprises reacting a compound of the formula

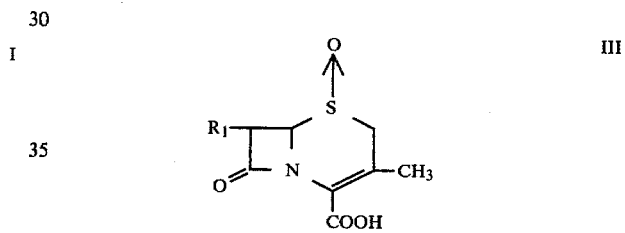

wherein $R_1$ is as hereinbefore defined with a compound to protect the carboxyl group with an easily removable group, brominating the latter to obtain a mixture of 3'-bromo and 2,3'-dibromo compounds of the formula

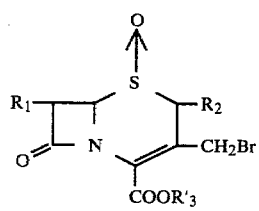

wherein $R_1$ and $R_2$ are as hereinbefore defined and $R_3'$ represents a carboxyl-protecting group, hydrolyzing the latter to form a compound of the formula

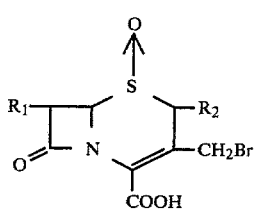

wherein $R_1$ and $R_2$ have the above definition and reacting the latter with a silylating agent of the formula

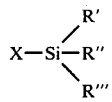

wherein R′, R″ and R‴ have the above definition and X is selected from the group consisting of halogen and

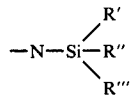

to form the corresponding compound of formula I.

The compounds of formula III are preferably reacted with tert-butanol to form the corresponding tert.-butyl ester but other easily hydrolyzable groups may also be used. The bromination is preferably effected with N-bromosuccinimide in an organic solvent with irradiation, with ultraviolet or visible light.

The ratio between the 3′-bromo and the 2,3′-dibromo-substituted products in the reaction mixture is determined by the starting materials and by the other conditions applied during the bromination reaction. The bromo-substituted products can be separated from the reaction mixture by for example, preparative high pressure chromatography on silica gel. If desired, the 2,3′-dibromo-substituted products can be converted (before, as well as after the separation from the bromination reaction mixture) into the corresponding 2-unsubstituted 3′-bromo-substituted compounds of formula IV wherein $R_2$ is hydrogen by the method described in the European application No. 78200174.7. The bromo-substituted products of formula IV wherein $R_1$ and $R_3'$ are defined as above and $R_2$ is hydrogen or bromine thus obtained can subsequently be hydrolyzed in known manner, for example with trifluoracetic acid.

In the following examples there are described several preferred embodiments to illustrate the invention. However, it is to be understood that the invention is not intended to be limited to the specific embodiments. Unless indicated otherwise, the IR-spectra were recorded as dispersions in KBr. The NMR-spectra have been measured at 60 MHz (unless stated otherwise), using tetramethyl silane as an internal standard; chemical shifts are indicated in δ values.

EXAMPLE 1

STEP A

A mixture of 103.2 g of dicyclohexylcarbodiimide, 43.5 g of t-butanol and 1.1 g of cuprous chloride was stored for 3 days at room temperature and the resulting compound was dissolved into 200 ml of dichloromethane. The solution was added dropwise to a stirred suspension of 35 g of 7-benzamido-3-methyl-3-cephem-4-carboxylic acid-1-oxide in 500 ml of dichloromethane and after stirring at room temperature for 24 hours, the obtained N,N′-dicyclohexyl urea was separated by filtration and washed with dichloromethane. The combined filtrate and washing liquid were extracted with a 2 N hydrochloric acid solution, a saturated sodium bicarbonate solution and twice with water. The dichloromethane was evaporated under vacuo and toluene was added to the residue. The obtained crystals were filtered off and were washed with toluene. After crystallization from a mixture of dichloromethane and toluene, 19.6 g of t-butyl 7-benzamido-3-methyl-3-cephem-4-carboxylate-1-oxide were obtained having the following characteristics:

PMR Spectrum (CDCl$_3$): 1.56 (s, 9H); 2.14 (s, 3H); 3.11; 3.41; 3.52; 3.83 (ABq, 2H, J 18.5 Hz); 4.65 (br., 1H); 6.25 (dd, 1H, J 4.5 and 9.5 Hz); 7.37–7.97 (m, 5H); 7.56 (d, 1H, J 9.5 Hz).

IR Spectrum: 3400, 1770, 1715, 1685, 1520, 1030 cm$^{-1}$.

STEP B

A solution of 40 g of t-butyl 7-benzamido-3-methyl-3-cephem-4-carboxylate-1-oxide in 2 liters of a 1:1 mixture of dichloromethane and acetic acid was cooled in an ice-bath and under exposure to light of two tungsten lamps of 150 W, bromination was effected with a total amount of 28 g of N-bromosuccinimide, which was added portionwise over about two hours. The exposure was continued for 3 hours and the obtained reaction mixture was washed with water three times and then with a saturated solution of sodium bicarbonate and again with water. The organic phase was treated with 5 g of activated charcoal and then was dried over magnesium sulfate, and filtered. The filtrate was distilled to dryness under vacuo and the residue consisting mainly of a mixture of the compounds mentioned below, was separated into its components with preparative high pressure chromatography over silica gel, using as eluent a mixture of dichloromethane and acetone (12:1). The components obtained were 10.4 g of t-butyl 7-benzamido-3-bromomethyl-3-cephem-4-carboxylate-1-oxide.

PMR Spectrum (CDCl$_3$+DMSO-D$_6$): 1.57 (s, 9H); 3.44; 3.74; 3.79; 4.09 (ABq, 2H, J 18 Hz); 4.26; 4.42; 4.51; 4.67 (ABq, 2H, J 10.5 Hz); 4.90 (d, 1H, J 4.8 Hz); 6.20 (dd, 1H, J 4.8 and 9.5 Hz); 7.35–7.96 (m, 5H); 7.85 (d, 1H, J 9.5 Hz).

IR Spectrum: 3330, 1795, 1715, 1645, 1520, 1030 cm$^{-1}$ and 8.7 g of t-butyl 7-benzamido-2-bromo-3-bromomethyl-3-cephem-4-carboxylate-1-oxide.

PMR Spectrum (CDCl$_3$+DMSO-D$_6$): 1.59 (s, 1H); 4.17; 4.34; 4.58; 4.75 (ABq, 2H, J 10.5 Hz); 5.34 (d, 1H, J 5 Hz); 5.73 (s, 2H); 6.35 (dd, 1H, J 5 and 9.5 Hz); about 7.34–7.98 (m, 5H); 7.71 (d, 1H, J 9.5 Hz).

IR Spectrum: 3380, 1790, 1725, 1680, 1520, 1050 cm$^{-1}$.

STEP C 6.25 g of t-butyl 7-benzamido-3-bromomethyl-3-cephem-4-carboxylate-1-oxide were added to 25 ml of trifluoroacetic acid at room temperature and after stirring for 15 minutes at room temperature, the trifluoroacetic acid was evaporated under vacuo. After addition of 20 ml of dichloromethane, evaporation to dryness was repeated. 25 ml of ether were added to the residue and the formed crystals were vacuum filtered, washed with ether and dried under vacuo to obtain 5.77 g of 7-benzamido-3-bromomethyl-3-cephem-4-carboxylic acid-1-oxide as a slightly yellowish colored solid having the following characteristics:

PMR Spectrum (DMSO-D$_6$): 3.95 (s, 2H); 4.49; 4.78 (ABq, 2H, J 10 Hz); 5.13 (d, 1H, J 4.5 Hz); 6.14 (dd, 1H, J 4.5 and 8 Hz); 7.4–8.1 (m, 5H); 8.56 (d, 1H, J 8 Hz).

IR Spectrum: 3385, 3280, 2550, 1785, 1720, 1642, 1605, 1580, 1515, 998 cm$^{-1}$.

STEP D

A mixture of 12.5 g of t-butyl 7-benzamido-2-bromo-3-bromomethyl-3-cephem-4-carboxylate-1-oxide and 50 ml of trifluoroacetic acid was stirred at room temperature for 15 minutes and was then evaporated to dryness under vacuo. 25 ml of dichloromethane were added to the residue and evaporation to dryness was repeated. A 1:1 mixture of ether and heptane was added to the residue and the formed crystals were vacuum filtered and washed with the same mixture to obtain 9.6 g of 7-benzamido-2-bromo-3-bromomethyl-3-cephem-4-carboxylic acid-1-oxide as an almost colorless solid, having the following characteristics:

PMR Spectrum (DMSO-D$_6$): 4.55 (s, 2H); 5.52 (d, 1H, J 5.2 Hz); 6.18 (dd, 2H, J 5.2 and 7.5 Hz); 6.20 (s, 1H); about 7.4–8.1 (m, 5H); 8.90 (d, 1H, J 7.5 Hz).

IR Spectrum: 3400, 3315, 2565, 1800, 1725, 1660, 1620, 1600, 1580, 1515, 1052, 997 cm$^{-1}$.

STEP E 258 mg of hexamethyldisilazane were added to a suspension of 0.97 g of 7-benzamido-3-bromomethyl-3-cephem-4-carboxylic acid-1-oxide in 30 ml of dry dichloromethane under a nitrogen atmosphere and the temperature of the mixture was kept at 20° C. by a water-bath. After 2 hours of stirring, the slightly brown colored solution was evaporated to dryness and the volatile components were removed at a pressure of 0.5 mm of mercury to obtain 1.05 g of trimethylsilyl 7-benzamido-3-bromomethyl-3-cephem-4-carboxylate-1-oxide having the following characteristics:

PMR Spectrum (CDCl$_3$): 0.39 (s, 9H); 3.47; 3.95 (ABq, 2H, J 18.7 Hz); 4.31; 4.93 (ABq, 2H, J 10.5 Hz); 4.71 (d, 1H, J 4.5 Hz); 6.37 (dd, 1H, J 4.5 and 9.5 Hz); 7.2–8.0 (m, 6H).

IR Spectrum (CHCl$_3$): 3410, 1806, 1712, 1675, 1250, 1058, 1045, 843 cm$^{-1}$.

STEP F 94 mg of hexamethyldisilazine in 6 ml of toluene were dropwise added at room temperature over 15 minutes to a suspension of 0.29 g of 7-benzamido-2-bromo-3-bromomethyl-3-cephem-4-carboxylic acid-1-oxide in 10 ml of toluene kept under a pressure of 5 cm of mercury. The mixture was then stirred for 1.5 hours under the same conditions whereafter the toluene was evaporated at a pressure of 0.5 mm of mercury to obtain 0.31 g of trimethylsilyl 7-benzamido-2-bromo-3-bromomethyl-3-cephem-4-carboxylate-1-oxide as a yellow brown colored solid having the following characteristics:

PMR Spectrum (CDCl$_3$): 0.39 (s, 9H); 4.26; 4.84 (ABq, 2H J 10 Hz); 5.39 (d, 1H, J 4.5 Hz); 5.72 (s, 1H); 6.46 (dd, 1H, J 4.5 and 9.5 Hz); 7.3–8.0 (m, 6H).

IR Spectrum (CHCl$_3$): 3420, 1810, 1712, 1678, 1253, 1053, 1010, 850 cm$^{-1}$.

EXAMPLE 2

STEP A 27 g of N-bromosuccinimide were added portionwise to an ice-cold solution of 30 g of t-butyl 7-formamido-3-methyl-3-cephem-4-carboxylate-1-oxide in 1600 ml of a 1:1 mixture of acetic acid and dichloromethane under exposure to light of two tungsten lamps of 150 W over 3 hours. After a total exposure of 4 hours, the reaction mixture was then washed 3 times with water, a saturated solution of sodium bicarbonate and again with water. The organic phase was treated with activated carbon, dried over magnesium sulfate and evaporated to dryness after filtration. The residue was subjected to preparative high pressure chromatography using a 4:1 mixture of dichloromethane and acetone as eluent to obtain by evaporation to dryness of the suitable fractions 10.7 g of t-butyl 3-bromomethyl-7-formamido-3-cephem-4-carboxylate-1-oxide having the following characteristics:

PMR Spectrum (CDCl$_3$ + a trace of DMSO-D$_6$): 1.54 (s, 9H); 3.78 (s, 2H); 4.38 and 4.65 (ABq, 2H, J 10 Hz); 4.90 (d, 1H, J 5 Hz); 5.99 (dd, 1H, J 5 and 9.5 Hz); 8.22 (d, 1H, J 9.5 Hz); 8.30 (s, 1H).

IR Spectrum: 3310, 1785, 1720, 1690, 1520, 1025 cm$^{-1}$ and 12.7 g of t-butyl 2-bromo-3-bromomethyl-7-formamido-3-cephem-4-carboxylate-1-oxide having the following characteristics:

PMR Spectrum (CDCl$_3$ + DMSO-D$_6$; 300 MHz): 1.57 (s, 9H); 4.35; 4.38; 4.61; 4.65 (ABq, 2H, J 10.5 Hz); 5.35 (d, 1H, J 5 Hz); 5.90 (s, 1H); 6.14 (dd, 1H, J 5 and 9 Hz); 8.28 (s, 1H); 8.46 (d, 1H, J 9 Hz).

IR Spectrum: 3280, 1805, 1730, 1690, 1510, 1060 cm$^{-1}$.

STEP B 10 g of t-butyl 3-bromomethyl-7-formamido-3-cephem-4-carboxylate-1-oxide in 40 ml of trifluoroacetic acid were stirred for 15 minutes at room temperature and after evaporation to dryness under vacuo, 25 ml of dichloromethane were added to the residue and evaporation to dryness was repeated. Ether was added to the residue and the formed crystals were vacuum filtered and washed with ether and the almost colorless solid was dried under vacuo to obtain 8.54 g of 3-bromomethyl-7-formamido-3-cephem-4-carboxylic acid-1-oxide having the following characteristics:

PMR Spectrum (DMSO-D$_6$): 3.88 (s, 2H); 4.47; 4.77 (AB q, 2H, J 9.8 Hz); 5.00 (d, 1H, J 4.5 Hz); 6.01 (dd, 1H, J 5.2 and 9.5 Hz); 8.25 (s, 1H); 8.48 (d, 1H, J 9.5 Hz); 10.60 (s, 1H).

IR Spectrum: 3292, 2635, 2580, 1787, 1719, 1650, 1528, 1002, 993 cm$^{-1}$.

STEP C 10 g of t-butyl 2-bromo-3-bromomethyl-7-formamido-3-cephem-4-carboxylate-1-oxide in 40 ml of trifluoroacetic acid were stirred for 15 minutes at room temperature and the solvent was removed by evaporation under vacuo. 25 ml of dichloromethane were added to the residue and evaporation to dryness was repeated. A 1:1 mixture of heptane and ether was added to the residue whereafter the slightly yellow crystals were vacuum filtered and were washed with the same solvent mixture to obtain 9.57 g of 2-bromo-3-bromomethyl-7-formamido-3-cephem-4-carboxylic acid-1-oxide having the following characteristics:

PMR Spectrum (DMSO-D$_6$): 4.55 (s, 2H); 5.45 (d, 1H, J 5.3 Hz); 6.13 (dd, 1H, J 5.3 and 9 Hz); 6.23 (s, 1H); 8.25 (s, 1H); 8.67 (d, 1H, J 9 Hz); 11.03 (s, 1H).

IR Spectrum: 3350, 2920, 2550, 1800, 1725, 1685, 1510, 1059, 993 cm$^{-1}$.

STEP D

Using the procedure of Step E of Example 1, 0.60 g of 3-bromomethyl-7-formamido-3-cephem-4-carboxylic acid-1-oxide was reacted with 265 mg of hexamethyldisilazane to obtain 640 mg of trimethylsilyl 3- bromomethyl-7-formamido-3-cephem-4-carboxylate-1-oxide by stirring for 2.25 hours at room temperature.

PMR Spectrum (CDCl$_3$): 0.39 (s, 9H); 3.49; 3.96 (ABq, 2H, J 18 Hz); 4.34; 4.86 (ABq, 2H, J 10 Hz); 4.60 (d, 1H, J 4.5 Hz); 6.18 (dd, 1H, J 4.5 and 10.5 Hz); 7.25 (d, 1H, J 10.5 Hz); 8.42 (s, 1H).

IR Spectrum (CHCl$_3$): 3498, 1802, 1700, 1252, 1055, 1045, 850 cm$^{-1}$.

STEP E

A solution of 82 mg of hexamethyldisilazane in toluene was dropwise added to a suspension of 244 mg of 2-bromo-3-bromomethyl-7-formamido-3-cephem-4-carboxylic acid-1-oxide in 10 ml of dry toluene kept under a pressure of 5 cm of mercury by means of an oil-pump over one hour and the reaction mixture was kept at 20° C. with a water-bath. After the addition of the hexamethyldisilazane was complete, stirring was continued for one hour under the same conditions, whereafter the mixture was evaporated to dryness at a pressure of 0.5 mm of mercury to obtain 220 mg of a slightly yellow-brown colored solid. The PMR- and IR-Spectrum were in agreement with the structure of trimethylsilyl 2-bromo-3-bromomethyl-7-formamido-3-cephem-4-carboxylate-1-oxide.

PMR Spectrum (CDCl$_3$): 0.43 (s, 9H); 4.30; 4.90 (ABq, 2H, J 10.5 Hz); 5.33 (d, 1H, J 5 Hz); 5.73 (s, 1H); 6.32 (dd, 1H, J 5 and 9 Hz); 7.08 (d, 1H, J 9 Hz); 8.47 (s, 1H).

IR Spectrum (CHCl$_3$): 3400, 1811, 1709, 1252, 1053, 999, 848 cm$^{-1}$.

EXAMPLE 3

STEP A 3.05 g of N-bromosuccinimide were added portionwise over 1.75 hours to an ice-cold solution of 4.6 g of t-butyl 2-bromo-3-methyl-7-phenylacetamido-3-cephem-4-carboxylate-1-oxide in 350 ml of dichloromethane under the exposure to light of a tungsten lamp of 150 W. After the addition of N-bromosuccinimide was complete, the exposure was continued for one hour and the orange colored solution was evaporated to dryness under vacuo at low temperature. The residue was chromatographed over silica gel, using as initial eluent a 72:1 mixture of methylene chloride and acetone and then a 49:1 mixture of the same components to obtain 1.4 g of t-butyl 2-bromo-3-bromomethyl-7-phenylacetamido-3-cephem-4-carboxylate-1-oxide by evaporation to dryness of the suitable fractions.

PMR Spectrum (CDCl$_3$): 1.55 (s, 9H); 3.58 (s, 2H); 4.16; 4.61 (ABq, 2H, J 11 Hz); 5.10 (d, 1H, J 5 Hz); 5.52 (s, 1H); 6.07 (dd, 1H, J 5 and 10 Hz); 6.76 (d, 1H, J 10 Hz); 7.26 (s, 5H).

IR Spectrum: 3350, 3260, 1790, 1705, 1670, 1500, 1060 cm$^{-1}$.

STEP B

A solution of 5.6 g of t-butyl 2-bromo-3-bromomethyl-7-phenylacetamido-3-cephem-4-carboxylate-1-oxide in 40 ml of trifluoroacetic acid was stirred for 15 minutes at room temperature and the solvent was removed under vacuo. Ether was added to the residue, whereafter the evaporation to dryness was repeated. After addition of ether, the crystals were collected by filtration to obtain 4.72 g of 2-bromo-3-bromomethyl-7-phenylacetamido-3-cephem-4-carboxylic acid-1-oxide as a slightly yellow solid having the following characteristics:

PMR Spectrum (DMSO-D$_6$): 3.60 (s, 2H); 4.46 (s, 2H); 5.29 (d, 1H, J 4.5 Hz); 5.87 (dd, 1H, J 4.5 and 7.5 Hz); 6.09 (s, 1H); 7.20 (s, 5H); 8.53 (d, 1H, J 7.5 Hz).

IR Spectrum: 3340, 1790, 1730, 1705, 1620, 1525, 1040 cm$^{-1}$.

STEP C

A solution of 37.3 g of t-butyl 3-bromomethyl-7-phenylacetamido-3-cephem-4-carboxylate-1-oxide in 130 ml of trifluoroacetic acid was stirred for 15 minutes at room temperature and then the solvent was removed by evaporation under vacuo. After addition of 100 ml of 1,2-dichloroethane, evaporation to dryness was repeated. Ether was added to the residue and the crystals were vacuum filtered, washed with ether and dried under vacuo to obtain 33.7 g of 3-bromomethyl-7-phenylacetamido-3-cephem-4-carboxylic acid-1-oxide as an almost colorless solid having the following characteristics:

PMR Spectrum (DMSO-D$_6$): 3.52 and 3.80 (ABq, 2H, J 14.5 Hz); 3.85 (s, 2H); 4.46, 4.79 (ABq, 2H, J 10 Hz); 4.95 (d, 1H, J 4.5 Hz); 5.83 (dd, 1H, J 4.5 and 8 Hz); 7.33 (m, 5H); 8.42 (d, 1H, J 8 Hz).

IR Spectrum: 3280, 3035, 1788, 1755, 1730, 1660, 1638, 1530, 1498, 1454, 1001, 709 cm$^{-1}$.

STEP D 258 mg of hexamethyldisilazane were added at room temperature to a suspension of 1.00 g of 3-bromomethyl-7-phenylacetamido-3-cephem-4-carboxylic acid-1-oxide in 30 ml of dry dichloromethane substantially free of alcohol under a nitrogen stream and after 20 minutes, a clear, slightly brown colored solution was obtained. The nitrogen atmosphere was sustained to a total amount of 2 hours, whereafter the solvent and other volatile components were removed at a pressure of 0.5 mm of mercury to obtain 1.14 g of trimethylsilyl 3-bromomethyl-7-phenylacetamido-3-cephem-4-carboxylate-1-oxide as a yellow brown powder having the following characteristics:

PMR Spectrum (CDCl$_3$): 0.30 (s, 9H); 3.31, 3.72 (ABq, 2H, J 18 Hz); 3.57 (s, 2H); 4.20, 4.75 (ABq, 2H, J 10.5 Hz); 4.43 (d, 1H, J 4.5 Hz); 6.00 (dd, 1H, J 4.5 and 9 Hz); 6.95 (d, 1H, J 9 Hz); 7.27 (s, 5H).

IR Spectrum (CHCl$_3$): 3400, 3275, 1803, 1768, 1709, 1690, 1055, 1048, 848 cm$^{-1}$.

STEP E

Using the procedure of Step E of Example 2, 0.33 g of trimethylsilyl 2-bromo-3-bromomethyl-7-phenylacetamido-3-cephem-4-carboxylate-1-oxide were obtained as a slightly brown colored solid from 0.30 g of 2-bromo-3-bromomethyl-7-phenylacetamido-3-cephem-4-carboxylic acid 1-oxide and 107 mg of hexamethyldisilazane.

PMR Spectrum (CDCl$_3$): 0.36 (s, 9H); 3.64 (s, 2H); 4.20 and 4.78 (ABq, 2H, J 10.5 Hz); 5.17 (d, 1H, J 4.5 Hz); 5.58 (s, 1H); 6.17 (dd, 1H, J 4.5 and 9.5 Hz); 6.78 (d, 1H, J 9.5 Hz); 7.34 (s, 5H).

IR Spectrum (CHCl$_3$): 3400, 1809, 1710, 1685, 1380, 1055, 998, 843 cm$^{-1}$.

EXAMPLE 4

STEP A

A solution of 21.8 g of t-butyl 3-methyl-7-phenoxyacetamido-3-cephem-4-carboxylate-1-oxide in a mixture of 500 ml of dichloromethane and 500 ml of acetic acid under a nitrogen atmosphere was cooled in an ice-bath and exposed to the light of a tungsten lamp of 150 W and 9.7 g of N-bromosuccinimide were added thereto. The mixture was exposed for 1.5 hours and then the reaction mixture was subsequently washed twice with 1.5 l of water, 0.5 l of a saturated sodium bicarbonate solution and with 1 l of water. The organic phase was dried over magnesium sulfate and after filtration concentrated by evaporation to a volume of about 50 ml. 3.2 g of t-butyl 2-bromo-3-bromomethyl-7-phenoxyacetamido-3-cephem-4-carboxylate-1-oxide were obtained by high pressure chromatography over silica gel and using as eluent a 12:1 mixture of dichloromethane and acetone followed by evaporation to dryness of the suitable fractions.

PMR Spectrum ($CDCl_3$): 1.58 (s, 9H); 4.23, 4.71 (ABq, 2H, J 10.5 Hz); 4.61 (s, 2H); 5.26 (d, 1H, J 5 Hz); 5.62 (s, 1H); 6.29 (dd, 1H, J 5 and 10.5 Hz); 6.8–7.6 (m, 5H); 7.90 (d, 1H, J 10.5 Hz).

IR Spectrum ($CHCl_3$): 3385, 1810, 1727, 1703, 1505, 1490, 1380, 1370, 1150, 1060, 1000 $cm^{-1}$.

After evaporation of subsequent fractions 5.5 g of t-butyl 3-bromomethyl-7-phenoxyacetamido-3-cephem-4-carboxylate-1-oxide were obtained having the following characteristics:

PMR Spectrum ($CDCl_3$+DMSO-$D_6$): 1.55 (s, 9H); 3.81 (s, 2H); 4.48 (s, 2H); 4.60 (s, 2H); 4.97 (d, 1H, J 4.5 Hz); 6.07 (dd, 1H, J 4.5 and 10 Hz); 6.8–7.5 (m, 5H); 8.08 (d, 1H, J 10 Hz).

IR Spectrum: 3365, 1790, 1720, 1695, 1520, 1065 $cm^{-1}$.

STEP B 1.2 g of t-butyl 2-bromo-3-bromomethyl-7-phenoxyacetamido-3-cephem-4-carboxylate-1-oxide were stirred in 8 ml of trifluoroacetic acid over 15 minutes and after evaporation to dryness under vacuo, 20 ml of 1,2-dichloroethane were added to the residue. The evaporation to dryness was repeated and 5 ml of ether and 50 ml of heptane were added to the residue. The obtained product was vacuum filtered and dried under vacuo to obtain 1.1 g of 2-bromo-3-bromomethyl-7-phenoxyacetamido-3-cephem-4-carboxylic acid-1-oxide as almost colorless crystals.

PMR Spectrum (DMSO-$D_6$): 4.39 and 4.57 (ABq, 2H, J 10 Hz); 4.66 (s, 2H); 5.40 (d, 1H, J 4.8 Hz); 6.11 (dd, 1H, J 4.8 and 9 Hz); 6.18 (s, 1H); 6.7–7.5 (m, 5H); 8.24 (d, 1H, J 9 Hz).

IR Spectrum: 3475, 1803, 1727, 1696, 1520, 1490, 1230, 1053, 996 $cm^{-1}$.

STEP C

Using the procedure of Step C of Example 3, 2.0 g of 3-bromomethyl-7-phenoxyacetamido-3-cephem-4-carboxylic acid-1-oxide were obtained from 2.3 g of t-butyl 3-bromomethyl-7-phenoxyacetamido-3-cephem-4-carboxylate-1-oxide. The said compound had the following characteristics:

PMR Spectrum (DMSO-$D_6$): 3.87 (s, 2H); 4.44 and 4.72 (ABq, 2H, J 10 Hz); 4.66 (s, 2H); 5.01 (d, 1H, J 4.8 Hz); 6.03 (dd, 1H, J 4.8 and 9.5 Hz); 6.8–7.5 (m, 5H); 8.11 (d, 2H, J 9.5 Hz); about 10.5 (s, broad, 1H).

IR Spectrum: 3275, 1780, 1770, 1722, 1675, 1530, 1233, 1218, 1175, 996 $cm^{-1}$.

STEP D

Using the procedure of Step D of Example 3, 600 mg of trimethylsilyl 3-bromomethyl-7-phenoxyacetamido-3-cephem-4-carboxylate-1-oxide were obtained from 525 mg of 3-bromomethyl-7-phenoxyacetamido-3-cephem-4-carboxylic acid-1-oxide and 138 mg of hexamethyldisilazane. The said compound had the following characteristics:

PMR Spectrum ($CDCl_3$): 0.35 (s, 9H); 3.35 and 3.82 (ABq, 2H, J 18.5 Hz); 4.25 and 4.72 (ABq, 2H, J 10.5 Hz); 4.50 (s and d, 3H); 6.08 (dd, 1H, J 4.5 and 9.8 Hz); 6.7–7.5 (m, 5H); 7.82 (d, 1H, J 9.8 Hz).

IR Spectrum ($CHCl_3$): 3380, 1807, 1702, 1388, 1372, 1255, 1062, 1050, 1003, 848 $cm^{-1}$.

STEP E

Using the procedure of Step E of Example 3, 300 mg of trimethylsilyl 2-bromo-3-bromomethyl-7-phenoxyacetamido-3-cephem-4-carboxylate-1-oxide were obtained as a slightly brown colored solid from 330 mg of 2-bromo-3-bromomethyl-7-phenoxyacetamido-3-cephem-4-carboxylic acid-1-oxide and 101 mg of hexamethyldisilazane. The said compound had the following characteristics:

PMR Spectrum ($CDCl_3$): 0.39 (s, 9H); 4.17 and 4.75 (ABq, 2H, J 10.5 Hz); 4.55 (s, 2H); 5.19 (d, 1H, J 5 Hz); 5.54 (s, 1H); 6.26 (dd, 1H, J 5 and 10 Hz); 6.7–7.5 (m, 5H); 7.77 (d, 1H, J 10 Hz).

IR Spectrum ($CHCl_3$): 3390, 1810, 1710, 1700, 1380, 1253, 1060, 1000, 848 $cm^{-1}$.

EXAMPLE 5

123 mg of tri-n-propylchlorosilane were added to a suspension of 312 mg of 7-benzamido-2-bromo-3-bromomethyl-3-cephem-4-carboxylic acid-1-oxide (prepared by the process of Step D of Example 1) in 25 ml of 1,2-dichloroethane under a nitrogen atmosphere and then a solution of 64 mg of triethyl-amine in 4 ml of 1,2-dichloroethane was dropwise added over 15 minutes under cooling in an ice-bath. The clear, slightly yellow colored solution was stirred for two hours at room temperature and after removal of the solvent under vacuo, 7 ml of diethyl ether was added. The obtained suspension was centrifuged and the clear liquid layer was separated and evaporated to dryness under vacuo. The residue was kept at a pressure of 0.5 mm of mercury for half an hour to obtain 210 mg of tri-n-propylsilyl 7-benzamido-2-bromo-3-bromomethyl-3-cephem-4-carboxylate-1-oxide having the following characteristics:

PMR Spectrum ($CDCl_3$): 0.4–1.7 (m, 21H); 4.24 and 4.72 (ABq, 2H, J 10.5 Hz); 5.30 (d, 1H, J 4.8 Hz); 5.65 (s, 1H); 6.33 (dd, 1H, 4.8 and 9.5 Hz); 7.1–7.8 (m, 6H).

IR Spectrum ($CHCl_3$): 3420, 1820, 1715, 1690, 1625, 1510, 1490, 1385, 1260, 1070, 1015, 840 $cm^{-1}$.

EXAMPLE 6

To a stirred suspension of 0.5 g of 7-benzamido-3-bromomethyl-3-cephem-4-carboxylic acid-1-oxide (prepared according to the process of Example 1, Step C) in 30 ml of 1:1 mixture of toluene and 1,2-dichloroethane, a solution of 188 mg of t-butyldimethyl-chlorosilane in the before mentioned solvent mixture was added under a nitrogen atmosphere at −10° C. and then a solution of 109 mg of triethylamine in 24 ml of the before mentioned solvent mixture was dropwise added over half an hour. Stirring was continued at −10° C. for 15 minutes and at 20° C. for 2 hours. After evaporation to dryness under vacuo, 10 ml of ether were added to the residue and the precipitate was separated by centrifugation.

The obtained liquor was evaporated to dryness and after drying the residue under a pressure of 0.5 mm of mercury, 0.1 g of t-butyldimethylsilyl 7-benzamido-3-bromomethyl-3-cephem-4-carboxylate-1-oxide were obtained having the following characteristics:

PMR Spectrum (CDCl$_3$): 0.38 (s, 6H); 0.97 (s, 9H); 3.45 and 3.92 (ABq, 2H, J 18 Hz); 4.24 and 4.86; 4.32 and 4.98 (2 ABq, 2H, J resp. 10.5 and 12 Hz); 4.67 (d, 1H, J 4.5 Hz); 6.27 (dd, 1H, J 4.5 and 9 Hz); 7.1–7.9 (m, 6H).

IR Spectrum(CHCl$_3$): 3410, 1805, 1710, 1675, 1630, 1505, 1485, 1385, 1260, 1050, 1005, 840 cm$^{-1}$.

EXAMPLE 7

Using the process of Example 5, 0.26 g of trihexylsilyl 3-bromomethyl-7-formamido-3-cephem-4-carboxylate-1-oxide were obtained by reaction of 0.35 g of 3-bromomethyl-7-formamido-3-cephem-4-carboxylic acid-1-oxide (prepared by the process of Step B of Example 2) with 0.33 g of trihexylchlorosilane and 0.1 g of triethylamine in 1,2-dichloroethane. The said compound had the following characteristics:

PMR Spectrum (CDCl$_3$): 0.3–1.8 (m, 39H); 3.38 and 3.85 (ABq, 2H, J 18 Hz); 4.15 and 4.84; 4.24 and 4.93 (2 ABq, 2H, J resp. 10.5 and 12 Hz); 4.52 (d, 1H, J 4.5 Hz); 5.83 (dd, 1H, J 4.5 and 9.5 Hz); 7.18 (d, 1H, J 9.5 Hz); 8.20 (s, 1H).

IR Spectrum (CHCl$_3$): 3400, 1805, 1700, 1625, 1080, 1060, 1005 cm$^{-1}$.

EXAMPLE 8

Using the process of Example 5, 0.18 g of t-butyldimethylsilyl 3-bromomethyl-7-phenoxyacetamido-3-cephem-4-carboxylate-1-oxide were obtained starting from 0.31 g of 3-bromomethyl-7-phenoxyacetamido-3-cephem-4-carboxylic acid-1-oxide (prepared by the process of Step C of Example 4), 90 mg of t-butyldimethylchlorosilane and 59 mg of triethylamine in 1,2-dichloroethane. The said compound had the following characteristics:

PMR Spectrum (CDCl$_3$): 0.36 (s, 6H); 0.95 (s, 9H); 3.35 and 3.82 (ABq, 2H, J 18 Hz); 4.25 and 4.63; 4.30 and 4.77 (2ABq, 2H, J resp. 10.5 and 12 Hz); 4.50 (s and d, 3H); 6.05 (dd, 1H, J 4.5 and 10 Hz); 6.7–7.4 (m, 5H); 7.85 (d, 1H, J 10 Hz).

IR Spectrum (CHCl$_3$): 3395, 1810, 1710, 1700, 1260, 1075, 1060, 1015, 840 cm$^{-1}$.

EXAMPLE 9

Using the process of Example 5, 0.12 g of chloromethyldimethylsilyl 3-bromomethyl-7-phenoxyacetamido-3-cephem-4-carboxylate-1-oxide were obtained starting from 0.40 g of 3-bromomethyl-7-phenoxyacetamido-3-cephem-4-carboxylic acid-1-oxide (prepared by the process of Step C of Example 4), 129 mg of chloromethyldimethyl-chlorosilane and 85 mg of triethylamine in 1,2-dichloroethane. The said compound had the following characteristics:

PMR Spectrum (CDCl$_3$+DMSO-D$_6$): 0.50 (s, 6H); 3.05 (s, 2H); 3.79 (s, broad, 2H); 4.42 and 4.73 (ABq, 2H, J 10.5 Hz); 4.56 (s, 2H); 4.90 (d, 1H, J 4.5 Hz); 6.06 (dd, 1H, J 4.5 and 10 Hz); 6.7–7.5 (m, 5H); 7.98 (d, 1H, J 10 Hz).

IR Spectrum (CHCl$_3$): 3390, 1810, 1705, 1260, 1080, 1020, 855 cm$^{-1}$.

Various modifications of the products and process of the invention may be made without departing from the spirit or scope thereof and it is to be understood that the invention is intended to be limited only as defined in the appended claims.

I claim:

1. Bromo-substituted deacetoxycephalosporins of the formula

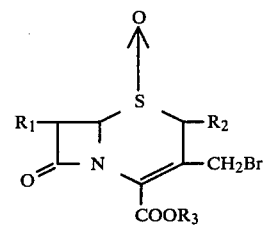

wherein R$_1$ is selected from the group consisting of benzamido, formamido, phenylacetamido and phenoxyacetamido, R$_2$ is selected from the group consisting of hydrogen and bromine and R$_3$ is a silyl group of the formula

wherein R', R" and R''' are individually selected from the group consisting of alkyl of 1 to 6 carbon atoms, a halogen-substituted alkyl of 1 to 6 carbon atoms and phenyl.

2. A compound of claim 1 which is trimethylsilyl 7-benzamido-3-bromomethyl-3-cephem-4-carboxylate-1-oxide.

3. A compound of claim 1 which is trimethylsilyl 7-benzamido-2-bromo-3-bromomethyl-3-cephem-4-carboxylate-1-oxide.

4. A compound of claim 1 which is trimethylsilyl 3-bromomethyl-7-formamido-3-cephem-4-carboxylate-1-oxide.

5. A compound of claim 1 which is trimethylsilyl 2-bromo-3-bromomethyl-7-formamido-3-cephem-4-carboxylate-1-oxide.

6. A compound of claim 1 which is trimethylsilyl 3-bromomethyl-7-phenylacetamido-3-cephem-4-carboxylate-1-oxide.

7. A compound of claim 1 which is trimethylsilyl 2-bromo-3-bromomethyl-7-phenylacetamido-3-cephem-4-carboxylate-1-oxide.

8. A compound of claim 1 which is trimethylsilyl 3-bromomethyl-7-phenoxyacetamido-3-cephem-4-carboxylate-1-oxide.

9. A compound of claim 1 which is trimethylsilyl 2-bromo-3-bromomethyl-7-phenoxyacetamido-3-cephem-4-carboxylate-1-oxide.

10. A compound of claim 1 which is tri-n-propylsilyl 7-benzamido-2-bromo-3-bromomethyl-3-cephem-4-carboxylate-1-oxide.

11. A compound of claim 1 which is t-butyldimethylsilyl 7-benzamido-3-bromomethyl-3-cephem-4-carboxylate-1-oxide.

12. A compound of claim 1 which is trihexylsilyl 3-bromomethyl-7-formamido-3-cephem-4-carboxylate-1-oxide.

13. A compound of claim 1 which is t-butyldimethylsilyl 3-bromomethyl-7-phenoxyacetamido-3-cephem-4-carboxylate-1-oxide.

14. A compound of claim 1 which is chloromethyldimethylsilyl 3-bromomethyl-7-phenoxyacetamido-3-cephem-4-carboxylate-1-oxide.

* * * * *